(12) United States Patent
Bauer et al.

(10) Patent No.: US 9,719,908 B1
(45) Date of Patent: Aug. 1, 2017

(54) ELECTROFRACTURING TEST SYSTEM AND METHOD OF DETERMINING MATERIAL CHARACTERISTICS OF ELECTROFRACTURED MATERIAL SAMPLES

(71) Applicant: Sandia Corporation, Albuquerque, NM (US)

(72) Inventors: Stephen J. Bauer, Albuquerque, NM (US); Steven F. Glover, Albuquerque, NM (US); Tom Pfeifle, Albuquerque, NM (US); Jiann-Cherng Su, Albuquerque, NM (US); Kenneth Martin Williamson, Albuquerque, NM (US); Scott Thomas Broome, Santa Fe, NM (US); William Payton Gardner, Albuquerque, NM (US); Gary Pena, Albuquerque, NM (US)

(73) Assignee: Sandia Corporation, Albuquerque, NM (US)

(*) Notice: Subject to any disclaimer, the term of this patent is extended or adjusted under 35 U.S.C. 154(b) by 137 days.

(21) Appl. No.: 14/625,287

(22) Filed: Feb. 18, 2015

Related U.S. Application Data

(60) Provisional application No. 61/941,258, filed on Feb. 18, 2014.

(51) Int. Cl.
| | |
|---|---|
| *G01N 37/00* | (2006.01) |
| *G01N 15/08* | (2006.01) |
| *G01N 1/28* | (2006.01) |
| *G01N 1/10* | (2006.01) |

(52) U.S. Cl.
CPC ............. *G01N 15/082* (2013.01); *G01N 1/28* (2013.01); *G01N 2001/1062* (2013.01)

(58) Field of Classification Search
CPC .................................................. G01N 15/082
See application file for complete search history.

(56) References Cited

U.S. PATENT DOCUMENTS

| 4,033,843 A * | 7/1977 | Krikorian | ............... C23C 14/35 204/192.11 |
| 4,683,147 A * | 7/1987 | Eguchi | ..................... B05D 1/60 136/258 |
| 4,696,702 A * | 9/1987 | Ellis, Jr. | ................ H01L 31/075 136/258 |

(Continued)

FOREIGN PATENT DOCUMENTS

WO   WO 2010051282 A1 *  5/2010  ........... C03C 17/245

OTHER PUBLICATIONS

Bialecki et al, 1991. "Disintegration of Rock by High Voltage Pulse Discharge", 8th IEEE Intl Pulsed Power Conf, San Diego, CA.

(Continued)

*Primary Examiner* — Laura Martin
*Assistant Examiner* — Alex Devito
(74) *Attorney, Agent, or Firm* — Daniel J. Jenkins

(57) ABSTRACT

A device for electrofracturing a material sample and analyzing the material sample is disclosed. The device simulates an in situ electrofracturing environment so as to obtain electrofractured material characteristics representative of field applications while allowing permeability testing of the fractured sample under in situ conditions.

15 Claims, 4 Drawing Sheets

(56) References Cited

U.S. PATENT DOCUMENTS 4,734,451 A * 3/1988 Smith .................. B05B 7/1486
118/300
2009/0314630 A1* 12/2009 Ngadi .................... A23L 1/025
204/165

OTHER PUBLICATIONS

Boev et al, 1999. "Destruction of Granite and Concrete in Water with Pulse Electric Discharges", 12th IEEE Intl Pulsed Power Conf, Monterey, CA.

Cho et al, 2006. "Dynamic fragmentation of rock by high-voltage pulses", ARMA/USRMS 06-1118, 41st U.S. Symp on Rock Mechanics, Golden, CO, Jun. 17-21, 2006.

Goldfarb et al, 1997. "Removal of Surface Layer of Concrete by a Pulse-Periodical Discharge", 11th IEEE Intl Pulsed Power Conf, Baltimore, MD.

Hamelin et al, 1993. "Hard Rock Fragmentation with Pulsed Power", 9th IEEE Intl Pulsed Power Conf, Albuquerque, NM.

Klinkenberg, L.J. 1941. "The permeability of porous media to liquids and gases," API Drilling and Production Practice, 200-213.

Lee, M.Y., S.W Webb and D.R. Bronowski. 2003. "Development of Helium-Mass-Spectrometry-Permeameter for the Measurement of permeability of near-impermeable rock", SAND2003-1468J, prepared by Sandia National Laboratories, Albuquerque, NM.

Lisitsyn et al, 1999. "Drilling and Demolition of Rocks by Pulsed Power", 12th IEEE Intl Pulsed Power Conf, Monterey, CA.

Narahara et al, 2007. "Evaluation of Concrete Made From Recycled Coarse Aggregates by Pulsed Power Discharge", 16th IEEE Intl Pulsed Power Conf, Albuquerque, NM.

Reess et al, 2009. "Electrohydraulic Shock Wave Generation as a Means to Increase Intrinsic Permeability of Concrete", 17th IEEE Intl Pulsed Power Conf, Washington DC.

Rim et al, 1999. "An Electric-Blast System for Rock Fragmentation", 12th IEEE Intl Pulsed Power Conf, Monterey, CA.

Touryan et al, 1989. "Electrohydraulic Rock Fracturing by Pulsed Power Generated Focused Shocks", 7th IEEE Intl Pulsed Power Conf, Monterey, CA.

Wang et al, 2009. "Optimization of Discharge Condition for Recycling Aggregate by Pulsed Discharge Inside of Concrete", 17th IEEE Intl Pulsed Power Conf, Washington, DC.

Weise & Löffler, 1993. "Experimental Investigation of Rock Fractioning by Replacing Explosives with Electrically Generated Pressure Pulses", 9th IEEE Intl Pulsed Power Conf, Albuquerque, NM.

* cited by examiner

ELECTROFRACTURING TEST SYSTEM AND METHOD OF DETERMINING MATERIAL CHARACTERISTICS OF ELECTROFRACTURED MATERIAL SAMPLES

CROSS-REFERENCE TO RELATED APPLICATIONS

This application claims priority to U.S. Provisional Patent Application 61/941,258, entitled "PERMEABILITY MEASUREMENT SYSTEM AND SYSTEM FOR ELECTRO FRACTURING AT HIGH PRESSURE," filed Feb. 18, 2014, the specification thereof is incorporated herein by reference in the entirety.

STATEMENT OF GOVERNMENT INTEREST

The United States Government has rights in this invention pursuant to Contract No. DE-AC04-94AL85000 between the United States Department of Energy and Sandia Corporation, for the operation of the Sandia National Laboratories.

FIELD

The present disclosure is generally directed to a device and method for electrofracturing material samples and for determining characteristics of electro-fractured material samples. The present disclosure is more particularly directed to a device and method for measuring permeability of electrofractured material samples.

BACKGROUND

Electrofracturing is a method of dynamic fragmentation using high-voltage pulses applied to rock through a pair of electrodes. Fragmentation occurs through two general processes: 1) electrohydraulic shock and 2) internal breakdown inside bulk solid dielectrics. In the first process, electrical current is passed through water which generates a shock wave of sufficient magnitude to crush/fail the rock as the wave travels through it. In the second process, the electric current flows through the rock preferentially along mineral interfaces that then induce tensile and branching cracks at the boundary interfaces either by heating and differential expansion or by a shock wave induced by the electrical impulse itself.

Although significant research on electrofracturing of rock has been conducted, it has been limited primarily to laboratory investigations on small rock volumes (core plugs of only a few millimeters in length) at ambient stress and temperature conditions. However, prior test systems and methods cannot evaluate larger rock volumes while simulating in situ stress conditions typical of rock formations, and in particular, sedimentary reservoirs (e.g., shale gas).

The need remains, therefore, for a device and method for evaluating larger rock volumes for electrofractured characteristics while simulating in situ stress conditions typical of rock formations, and in particular, sedimentary reservoirs (e.g., shale gas).

SUMMARY OF THE DISCLOSURE

In an embodiment of the present invention, a device is disclosed that includes a pressure vessel comprising an internal cavity, a pressurized fluid supply system fluidly coupled to the internal cavity, a material sample disposed within the internal cavity, a voltage source electrically coupled to the material sample to provide a voltage pulse across the material sample, and a gas measurement system in fluid coupled to the material sample.

According to another embodiment, a method is disclosed that includes providing a material sample, subjecting the material sample to an external pressure, subjecting the material sample to a voltage potential, flowing a test fluid across the material sample, and measuring the amount of text gas that flows from the material sample.

An advantage of the present disclosure is to provide a system and method for determining the characteristics of material electrofractured under in situ stress conditions typical of rock formations.

Another advantage of the present disclosure is to provide a system that could potentially be used to evaluate and deploy near zero water resources for fracturing rock formations, and in particular, sedimentary reservoirs such as, but not limited to shale gas formations.

Other features and advantages of the present disclosure will be apparent from the following more detailed description of the preferred embodiment, taken in conjunction with the accompanying drawings which illustrate, by way of example, the principles of the disclosure.

BRIEF DESCRIPTION OF THE DRAWINGS

Wherever possible, the same reference numbers will be used throughout the drawings to represent the same parts.

DETAILED DESCRIPTION

The present invention now will be described more fully hereinafter with reference to the accompanying drawings, in which preferred embodiments of the invention are shown. This invention may, however, be embodied in many different forms and should not be construed as limited to the embodiments set forth herein; rather, these embodiments are provided so that this disclosure will be thorough and complete and will fully convey the scope of the invention to those skilled in the art.

The present disclosure is directed to a device for electrofracturing a material sample. The device simulates an in situ electrofracturing environment so as to obtain electrofractured material characteristics representative of field applications. The device is configured to allow for the flow of a fluid through the sample before, during and/or after electrofracturing so as to measure in real time the permeability of the sample. In this exemplary embodiment, the fluid is a gas. In other embodiments, the fluid may be a gas, liquid or combination thereof. In an embodiment, the liquid may be an aqueous based fluid.

Figure 1:
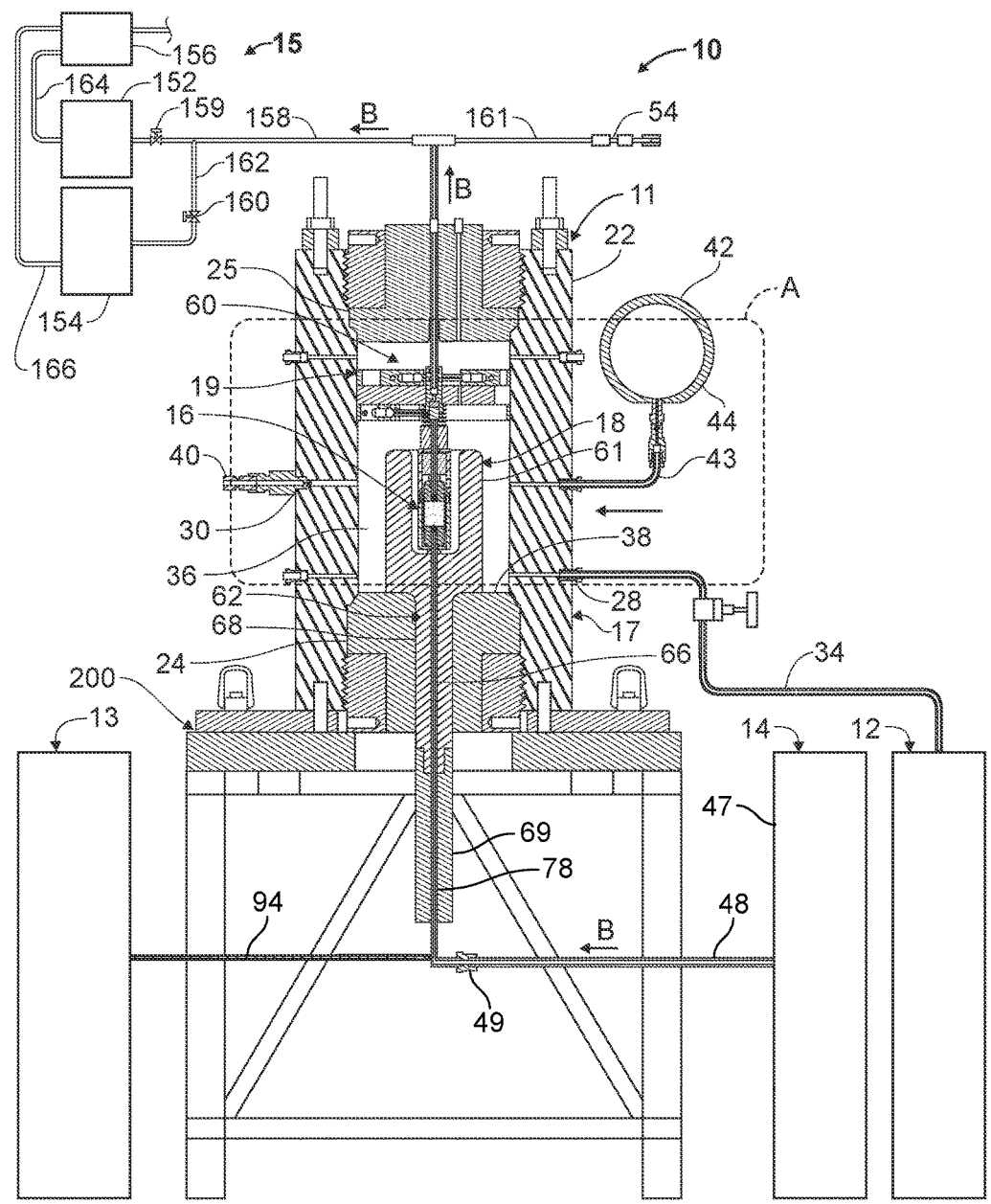
FIG. 1 is a schematic and illustration an embodiment of an electrofracturing test device system according to an embodiment of the disclosure

FIG. 1 illustrates an embodiment of an electrofracturing test system 10 according to an embodiment of the disclosure. The electrofracturing test system 10 includes an electrofracturing test device 11, a pressurized fluid supply system 12, a high voltage system 13, a gas supply system 14, a mass flow measurement system 15, and a test assembly 16. The electrofracturing test device 11 simulates the electrofracturing of a material sample 101 contained within the test assembly 16 under in situ geologic formation pressures. As can be seen in FIG. 1, the electrofracturing test device 11 is supported by a test device support structure 200. In this exemplary embodiment, the test device support structure 200 is a table, however, in other embodiments, the test device support structure 200 may be a table, stand, tower or other structure capable of providing support to the electrofracturing test device 11.

Figure 2:
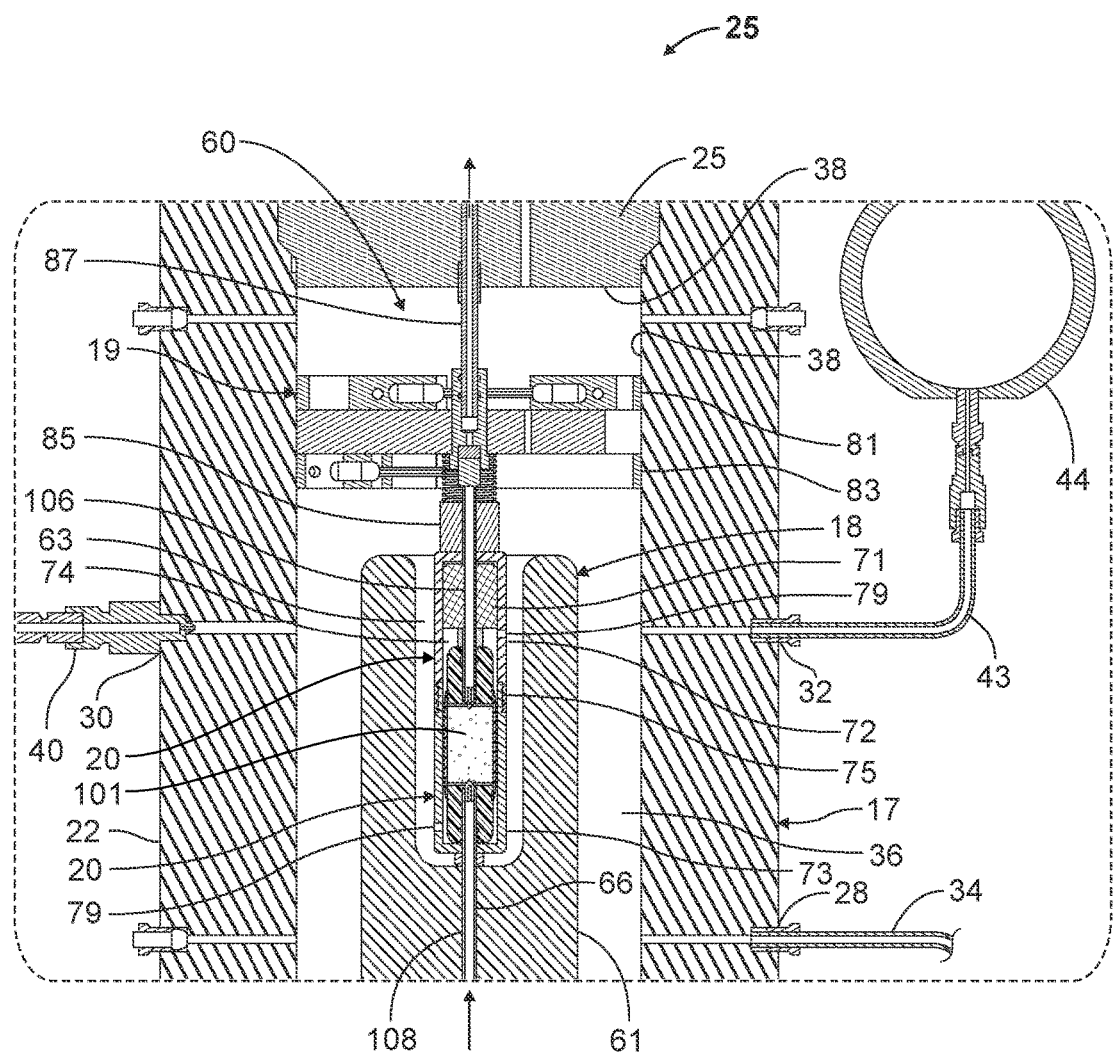
FIG. 2 illustrates an enlarged portion A of FIG. 1.

As can be seen in FIGS. 1 and 2, the electrofracturing test device 11 includes a pressure vessel 17 and a sample isolation assembly 60 disposed within the pressure vessel 17. The pressure vessel 17 includes an outer casing 22, a lower cap 24 and an upper cap 25. The outer casing 22 includes a pressure inlet 28, a pressure outlet 30 and a pressure monitoring port 32. The pressure inlet 28 is attached to the pressurized fluid supply system 12. The pressurized fluid supply system 12 is configured to provide a pressurized fluid from a pressurized fluid source (not show) through piping, controls and valving as necessary to supply and control a pressurized fluid to the pressure inlet 28. The pressure inlet 28 is in fluid connection with an inner chamber 36 of the pressure vessel 17 that is defined by chamber surfaces 38 of the outer casing 22, lower cap 24 and upper cap 26. The lower end cap 24 and/or the upper end cap 25 is separable from the outer casing 22 so as to allow the sample isolation assembly 60 and the test assembly 16 to be inserted and removed from the pressure vessel 17. In such a manner, the test assembly 16 may be inserted into the pressure vessel 17 before and after testing as well as during testing between applied voltages.

The pressurized fluid supply system 12 is capable of providing a pressurized fluid up to a pressure representative of a subterranean geologic formation. In an embodiment, the pressurized fluid supply system 12 is capable of providing a pressurized fluid up to 20,000 pounds per square inch (psi). In another embodiment, the pressurized fluid supply system 12 is capable of providing a pressurized fluid up to 15,000 psi. In another embodiment, the pressurized fluid supply system 12 is capable of providing a pressurized fluid up to 10,000 psi. In an embodiment, the pressurized fluid supply system 12 is capable of providing a pressurized fluid between atmospheric pressure and 20,000 psi. In an embodiment, the pressurized fluid supply system 12 is capable of providing a pressurized fluid between 14 psi and 20,000 psi. In an embodiment, the pressurized fluid supply system 12 is capable of providing a pressurized fluid between 1,000 psi to 20,000 psi. In an embodiment, the pressurized fluid supply system 12 is capable of providing a pressurized fluid between 2,000 psi to 20,000 psi. In an embodiment, the pressurized fluid supply system 12 is capable of providing a pressurized fluid between 2,000 psi to 15,000 psi.

The pressurized fluid provided by the pressurized fluid supply system 12 is a low compressibility or highly incompressible, nonconductive fluid. In an embodiment, the pressurized fluid may be selected from a group including, but not limited to, oils, hydraulic fluid, deionized water or other incompressible, nonconductive fluids. In an embodiment, the pressurized fluid may be transformer oil.

The pressure outlet 30 is in fluid connectivity with a pressure outlet conduit 40, which is in fluid connectivity with pressure outlet system (not shown) capable of receiving pressurized fluid discharged from the pressure vessel 17. The pressure outlet system includes piping, controls and valving necessary to receive and control a discharged pressurized fluid.

The pressure monitoring port 32 is fluidly connected to a pressure monitoring system 42. In this exemplary embodiment, the pressure monitoring system 42 includes a pressure monitor conduit 43 and a pressure gauge 44. In another embodiment, the pressure monitoring system 42 may be a pressure transducer with a conditioned electrical signal output such that recording of test confining pressures is possible with a data acquisition system.

The sample isolation assembly 60 includes an insulator assembly 18, an upper retention system 19 and a sample holder 20. The insulator assembly 18 includes an upper portion 61 and a lower portion 62. The upper portion or insulator body 61 includes an internal cavity 63 for receiving the sample holder 20. The insulator body 61 also includes an opening 64 at a first end 65 of the internal cavity 63 for receiving the sample holder 20. The insulator body 61 also includes a passage 66 at a second end 67 opposite the first end 65. The passage 66 extends through the insulator body 61 from the internal cavity 63 to the lower portion 62.

The lower portion 62 includes a first section 68 and a second section 69. In this exemplary embodiment, the first section 68 is formed with the insulator body 61 as a single unit. In another embodiment, the first section 68 may be formed of one or more separate material pieces. The passage 66 extends through the first and second sections 68, 69 to an external opening 70. The second conductor 108 of the test assembly 16 extends through the passage 66. The second section 69 includes a conductor extension 78. The conductor extension 78 is a conductive pipe or conduit that electrically connects the second conductor 108 of the test assembly 16 to the high voltage supply system 13 and fluidly connects the conductor extension of the test assembly 16 to the gas supply system 14. In another embodiment, the conductor extension 78 may be formed of one or more conductive pipes or conduits. In yet another embodiment, the conductor extension 78 may be omitted and the test assembly 16 may extend through the lower portion 62 to the high voltage supply system 13 and the gas supply system 14.

In this exemplary embodiment, the lower portion 62 includes two sections, however, in another embodiment, the lower portion may be formed of one or more sections. Also in this embodiment, the second section 69 is formed of a single section, however, in another embodiment, the second section 69 may be formed of one or more sections. The insulator assembly 18 is formed of an insulative material, such as, but not limited to ceramics, plastics, and polymers. In an embodiment, the insulator assembly 18 may be formed of a thermoplastic acetal homopolymer resin. In an embodiment, the thermoplastic acetal homopolymer resin may be a polyoxymethylene.

The sample holder 20 is a closed cylinder capable of being received and disposed within in the internal cavity 63 of the insulator assembly 18. The sample holder 20 includes a first portion 72 and a second portion 73 that are temporarily joined to form the closed cylinder having an internal cavity 74. The sample holder 20 contains a test assembly 16 in the internal cavity 74. The sample holder 20 is configured to be opened to facilitate sample removal during the testing process with no damage/alteration of the sample, but to allow for observational work to be performed, and then closed and re-inserted into test system. In this exemplary embodiment, the first and second portions 72, 73 are joined by threaded joint 75, however, in another embodiment, the first and second portions 72, 73 may be joined by another separable joining system and method, such as, but not limited to fasteners, snap fit arrangements, and bayonet arrangements. The first and second portions 72, 73 also include first and second openings 76, 77, respectively, for allowing passage of first and second conductors 102, 104 of the test assembly 16. The sample holder 20 also includes a spacer 71 for aligning and securing the test assembly 16 within the sample holder 20. The sample holder 20 includes fluid openings or fluid passages 79 for allowing pressurized fluid to move from the inner chamber 36 of the pressure vessel 17 to internal cavity 74 of the sample holder 20.

Referring to FIG. 2, the upper retention system 19 includes an upper clamp 81, lower clamp 83, a spacer 85 and a ground probe 87 for aligning and securing the test assembly 16 and sample holder 20 within the insulator assembly 18. In addition, the upper retention system 19 provides electrical ground from the test assembly 16 to the pressure vessel 17. The pressure vessel 17 is further grounded to a facilities ground (not shown). In addition, the upper retention system 19 includes seals, springs, clamps and other hardware to assist in aligning and securing the test assembly 16 and sample holder within the insulator assembly 18, as well as seals to seal the upper retention system 19 within the pressure vessel 17.

Referring again to FIGS. 1 and 2, the high voltage supply system 13 includes a high voltage supply 92 and a high voltage transmission line 94. The high voltage supply 92 includes a voltage source capable of electrofracturing a material sample. In an embodiment, the high voltage supply 92 includes two ±100 kilovolts (kV) DC power sources, a charge management network with charging relay and dump tank, and a pulse forming network with a selection of resistors, inductors, and capacitors required to achieve the desired pulse characteristics.

The high voltage transmission line 94 is in electrical connectivity with the electrofracturing test device 11. The high voltage supply system 13 is capable of providing a voltage capable of fracturing a material sample contained in the electrofracturing test device 11. In this exemplary embodiment, the high voltage supply system 13 is capable of delivering a voltage up to 200 kilovolts (kV). In an embodiment, the high voltage supply system 13 is capable of providing a voltage up to 1 MV. In another embodiment, the high voltage supply system 13 is capable of providing a voltage up to 300 kilovolts (kV). In an embodiment, the high voltage supply system 13 is capable of providing a voltage between 150 kV and 200 kV.

In addition, the high voltage supply system 13 is capable of providing a voltage having a pulse width of between 100 picoseconds (ps) to 1 day. In an embodiment, the high voltage supply system 13 is capable of providing a voltage having a pulse width of between 100 ps to 1 hour (hr). In an embodiment, the high voltage supply system 13 is capable of providing a voltage having a pulse width of between 1 nanosecond (ns) to 500 microseconds (μs). In an embodiment, the high voltage supply system 13 is capable of providing a voltage having a pulse width of between 1 ns to 10 μs.

In addition, the high voltage supply system 13 is capable of repeating a voltage pulse or cycling between pulses. In an embodiment, the time between pulses may be on the order of hours to days to allow for sample analysis outside of the electrofracturing test device 11. In an embodiment, the time between pulses may be between 100 μs to 1 day. In another embodiment, the time between pulses may be between 1 ms to 1 hr. In an embodiment, the time between pulses may be between 1 ms to 1 hr.

Further in addition, the high voltage supply system 13 is capable of providing various pulse shapes, such as, but not limited to sinusoidal, exponential and surge. The various pulse shapes may have various pulse parameters, such as width, ramp rate, oscillating frequency, dampening, available energy, decay rates and other pulse parameters.

The gas supply system 14 includes a gas supply 47, a gas feed line 48, a line couple 49 and various other gas supply system components, such as, but not limited to lines, gauges, valves (not shown) for controlling the supply of a test gas to the electrofracturing test device 11. The line couple 49 is used to connect and disconnect the gas feed line 48 to the electrofracturing test device 11. In such a manner, the line couple can be used to disconnect and mechanically electrically isolate the gas supply system 14 from the electrofracturing test device system 11. In another embodiment, non-conductive couples or isolators may be used to electrically isolate the gas supply system 14 from the electrofracturing test device system 11.

The test gas may be any gas of interest for the material test sample. In an embodiment, the test gas may be an inert gas, air, or other gas of interest for interacting with the material test sample contained in the electrofracturing test device 11. In an embodiment, the test gas may be selected from a group including, but not limited to helium, neon, argon, krypton, xenon, methane, ethane propane. In an embodiment, the test gas may be helium. In an embodiment, various test gas additives may be added to the test gas. In an embodiment, surfactants, lubricants and/or condensed phases such as water and/or water vapor may be added to the test gas. The test gas is provided to the electrofracturing text device 11 at a pressure of between greater than 0 psi and 100 psi. In an embodiment, the test gas is provided to the electrofracturing text device 11 at a pressure of between 14 psi and 50 psi. The test gas is provided to the electrofracturing text device 11 at a pressure of between 20 psi and 40 psi.

In another embodiment, the test gas may be provided between greater than 0 psi and up to less than the pressure within the pressure vessel 17. In an embodiment, the pressure may be between greater than 0 psi and up to 10,000 psi. In another embodiment, the pressure may be between greater than 0 psi and up to 4,000 psi. It should be understood that in these embodiments, a pressure regulation vessel (not shown) may be added to the electrofracturing test system 10 before the text gas is provided to the gas measurement system 15 so as to decrease the pressure provided by the gas measurement system components.

The gas measurement system 15 is capable of measuring gas flow rate and/or gas composition. The gas measurement system 15 includes a low flow detector 152, a flow detector 154 and a gas capture system 156. The gas measurement system 15 further includes a gas exit line 158 that fluidly connects the electrofracturing test device 11 with the gas measurement system 15. The gas measurement system also includes first and second flow control valves 159, 160 on the gas exit line 158 for directing gas flow to the low flow detector 152 or flow detector 154, respectively. The gas exit line 158 includes an auxiliary line 161 for allowing by-pass or venting of gas from electrofracturing test device 11.

The low flow detector 152 is a mass spectrometer, such as a gas detector, capable of detecting gas flow of greater than $10^{-8}$ cm$^3$/sec. In an embodiment, the low flow detector 152 is capable of detecting gas flow of less than $10^{-5}$ cm$^3$/sec. In an embodiment, the mass spectrometer may be a specific compound gas detector, such as, but not limited to a helium leak detector. In an embodiment the mass spectrometer may tunable to a variety of different gases ranging in molecular weight. As understood, mass spectrometers may be capable of identifying one or more molecules or compounds contained in the gas flow.

The flow detector 154 is a flow measurement device capable of detecting gas flow greater than 0.01 cc/sec. In an embodiment, the gas flow detector 154 is capable of measuring gas flow greater than 0.1 cc/sec. In an embodiment, the flow detector may be a mass or volume flow measurement gauge. In an embodiment, the flow detector 154 may be a selectable bank of flow detectors capable of measuring various ranges of gas flow.

Figure 3:
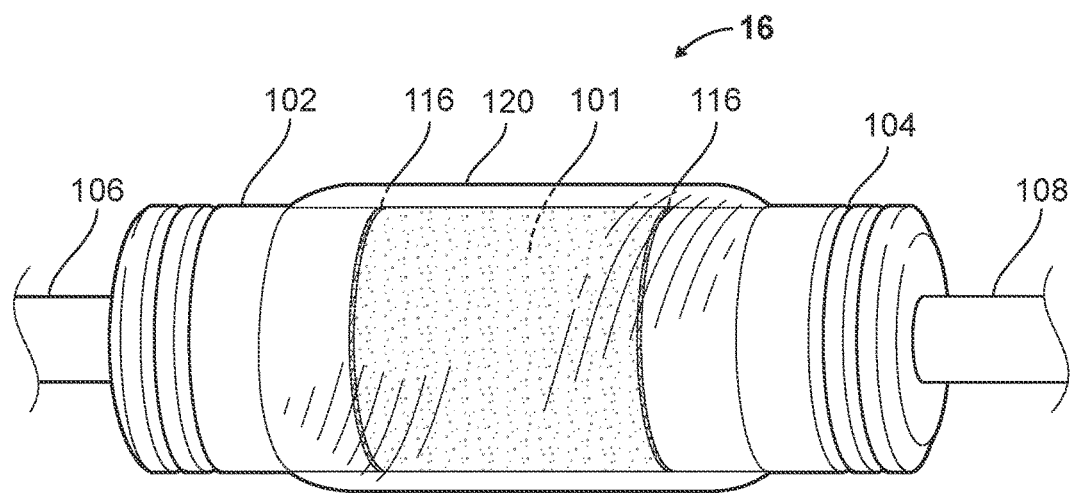
FIG. 3 is a partial perspective view illustrating an embodiment of a test assembly according to the disclosure.
Figure 4:
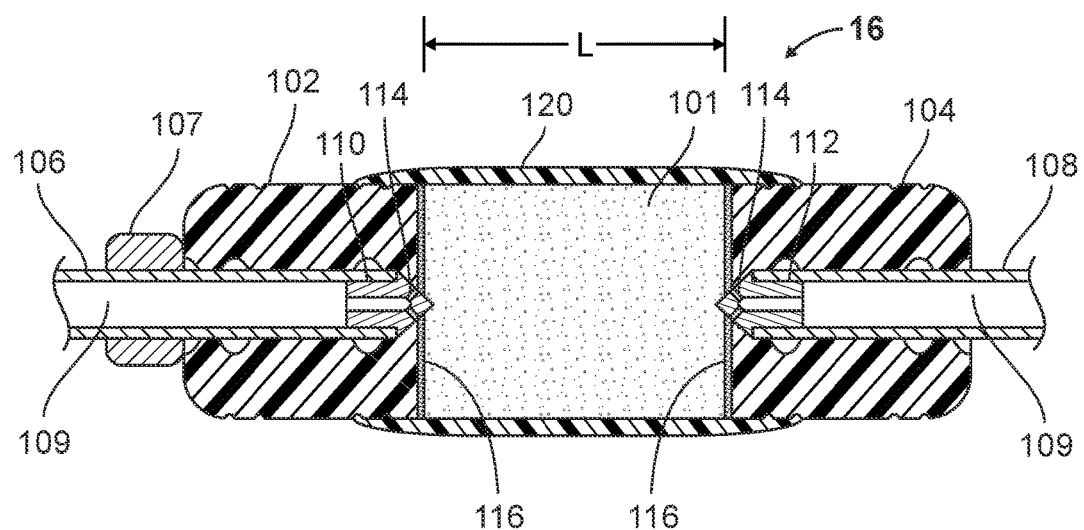
FIG. 4 is a cut away view of the test assembly of FIG. 3.

As can be seen in FIGS. 3 and 4, the test assembly 16 includes a material sample 101, a first end cap 102 and a second end cap 104 disposed on opposite ends of the material sample 101, a first conductor 106 and a second conductor 108 traversing through the first and second end caps 102, 104 to the material sample, respectively, and a jacketing material 120 surrounding the material sample. The first and second conductors 106, 108 include gas passages 109 for receiving a gas from the gas supply system 14 and providing the gas to the material sample 101. The first and second conductors 106, 108 include first and second conductor ends 110, 112 disposed at the sample ends thereof. The first and second conductor ends 110, 112 include gas ports 114 for directing a gas towards the material sample 101. The first conductor 106 includes a collar 107 for sample holding spacing such that a sample 101 with varying lengths L may be tested. The first and second conductors 106, 108 are formed of a conductive metal, such as, but not limited to steel, stainless steel, and other capable of performing in consideration of pressure, chemical, and other parameter considerations.

The first and second end caps 102, 104 are formed of an insulative material and align the first and second conductors 106, 108 with the material sample 101. The insulative material may be a ceramic, plastic, polymer or epoxy material having a high dielectric constant. In an embodiment, the first and second end caps 102, 104 may be formed of an engineered thermoplastic. In an embodiment, the thermoplastic may be polyoxymethylene.

The jacketing material 120 coats and seals the material sample 101 between the first and second end caps 102, 104 so as to form a sealed volume around the material sample 101. The jacketing material 120 is a flexible, deformable, impermeable to gas and oil, capable of maintaining its integrity to static and dynamic pressurizations. The jacketing material 120 may be selected from a group of flexible, deformable, impermeable and preferably transparent or translucent, transparent in computational tomography (CT) (for aiding in post-test analysis) materials, such as, but not limited to a polymer, plastic or epoxy material. In an embodiment, the jacketing material 120 may be a translucent epoxy, such as a ultraviolet curable polymer compound.

Between the material sample 101 and the first and second end caps 102, 104 are disposed insulative screens 116 to help disperse and collect the gas from across the face of the material sample 101. In an embodiment, the insulative screens 116 may be made of a ceramic, plastic, polymer, epoxy or organic material. In an embodiment, the insulative screens 116 may be made of polyether ether ketone (PEEK) cloth.

The material sample 101 may be an engineered, geologic or other material requiring electrofracturing. In an embodiment, the material sample may be of geologic origin such as but not limited to igneous, metamorphic, and sedimentary lithologies.

The material sample 101 has a length L as shown on FIG. 4. In this exemplary embodiment, the length L is between 3 cm to 9 cm. In another embodiment, the length L may be between 0.5 cm to 30 cm dependent upon the applied voltage, test material resistance, sample assembly size and scale. In this exemplary embodiment, the material sample 101 had a diameter of 15 cm. In another embodiment, the material sample 101 may have a diameter of between 12 cm and 15 cm. In another embodiment, the scale of the device may be modified to accept various lengths and diameters.

Figure 5:
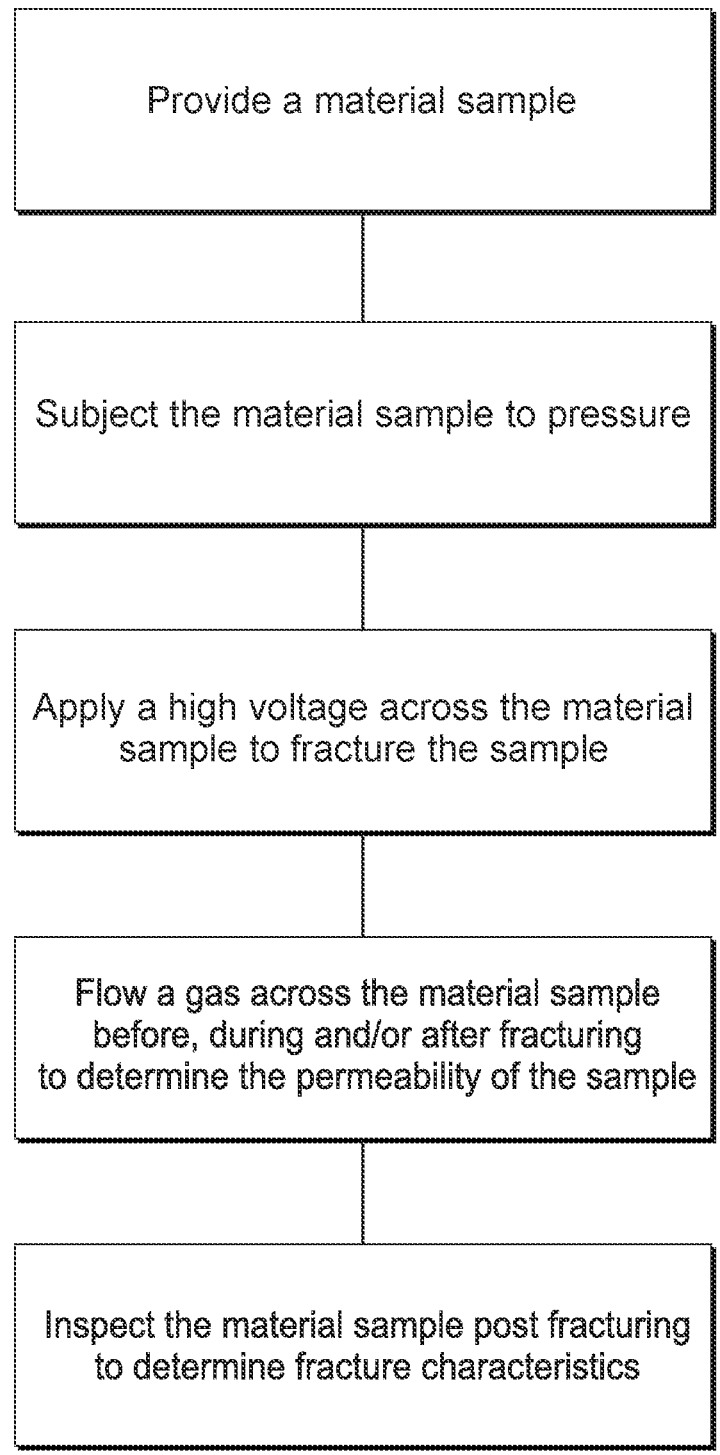
FIG. 5 is an embodiment of a method for electrofracturing and analyzing material samples.

The present disclosure is also directed to a method of testing a material sample by electrofracturing a material sample with high voltage while under high pressure, determining the permeability of the material sample, before, during and after electrofracturing, removing the material sample from the test device, and analyzing the material sample. According to an embodiment of the disclosure, a method of electrofracturing and testing a material sample, and as shown in FIG. 5, is disclosed that includes the following steps:

Provide a material sample

Subject the material sample to high pressure

Apply a high voltage across the material sample to fracture the sample

Flow a gas across the material sample before, during and/or after fracturing to determine the permeability of the sample Inspect the material sample post fracturing to determine fracture characteristics.

According to the present disclosure, the material sample may be engineered, geologic or other material requiring electrofracturing. In an embodiment, the material sample may be of geologic origin such as but not limited to igneous, metamorphic, and sedimentary lithologies.

The material sample is subjected up an applied pressure of up to 20,000 pounds per square inch (psi). In another embodiment, the applied pressure may be up to 15,000 psi. In another embodiment, the applied pressure may be up to 10,000 psi.

A voltage is applied across the material sample to electrofractured the material sample. The voltage is up to voltage up to 1 MV. In another embodiment, the voltage is up to 200 kV. In an embodiment, the voltage is between 150 kV and 200 kV. The applied voltage may have various pulse shapes, such as, but not limited to sinusoidal, exponential and surge. The various pulse shapes may have various pulse parameters, such as width, ramp rate, oscillating frequency, dampening, available energy, decay rates and other pulse parameters.

The high voltage supply system is capable of providing a voltage having a pulse width of between 100 picoseconds (ps) to 1 day. In an embodiment, the high voltage supply system 13 is capable of providing a voltage having a pulse width of between 100 ps to 1 hour (hr). In an embodiment, the high voltage supply system 13 is capable of providing a voltage having a pulse width of between 1 nanosecond (ns) to 500 microseconds (μs). In an embodiment, the high voltage supply system 13 is capable of providing a voltage having a pulse width of between 1 ns to 10 μs.

In addition, the high voltage supply system is capable of repeating a voltage pulse or cycling between pulses. In an embodiment, the time between pulses may be on the order of hours to days to allow for sample analysis outside of the electrofracturing test device. In an embodiment, the time between pulses may be between 100 μs to 1 day. In another embodiment, the time between pulses may be between 1 ms to 1 hr. In an embodiment, the time between pulses may be between 1 ms to 1 hr.

A gas is flowed across the material sample and the permeability of the sample is determined before, during and/or after fracturing to determine the permeability of the sample. A gas is provided at a pressure of between greater than 0 psi to 100 psi to a surface of the material sample, and is measured flowing from an opposite surface of the material sample to determine permeability. In such a manner the initial permeability of the material before fracturing can be determined, the permeability of the material sample during one or more electrofracturing cycles can be determined, and the permeability of the material sample after electrofracturing can be determined.

Because initial permeability is expected to be low and fracture permeability high, a wide dynamic range of measurement is needed. Low permeability measurements can be made relatively quickly using transient pressure pulse techniques, however, these techniques are not suited for high permeability media. Thus permeability was measured using steady state gas flow utilizing flow meters with sensitivity ranges from 10-10 ccatm/s to 100 ccatm/s. The text gas may be selected based on inert interaction with the material sample and/or small molecular size. In an embodiment, helium may be selected as the flowing gas due to its small molecular size, relatively low viscosity, and its ability to be used with helium leak detector mass spectrometers, which provide ultralow mass flow detection.

The viscous flow of compressible gas through a porous media ignoring gravity can be described by Darcy's equation:

$$q = \frac{k}{\mu} \nabla p, \qquad (1)$$

where q is the volumetric flux rate (m$^3$/m$^2$/s), k is the intrinsic permeability (m$^2$) and $\mu$ is the dynamic viscosity of the gas (Pa s). The integration of (1) given constant pressure boundary conditions ($p=p_{in}|x=0$; $p=p_{out}|x=L$) and assuming isothermal conditions, an ideal gas, constant compressibility and viscosity gives:

$$q_{sc} = \frac{kA}{2L\mu P_{sc}}(p_{in}^2 - p_{out}^2), \qquad (2)$$

where $q_{sc}$ is the volumetric flow at the core outlet at reference conditions (m$^3$-$_{sc}$/s, $P_{sc}$ is the reference pressure (1 atm), and A is the cross sectional area normal to the flow direction. Rearranging (2) for permeability gives:

$$k = \frac{q_{sc} 2L\mu P_{sc}}{A(p_{in}^2 - p_{out}^2)}. \qquad (3)$$

Equation (3) is used to calculate the apparent intrinsic viscous permeability given the measured flow rate and upstream and downstream pressures.

The test gas may be any gas of interest for the material test sample. In an embodiment, the test gas may be an inert gas, air, or other gas of interest for interacting with the material test sample contained in the electrofracturing test device 11. In an embodiment, the text gas may be selected from a group including, but not limited to helium, neon, argon, krypton, xenon, methane, and ethane propane. In an embodiment, the test gas may be helium. In an embodiment, various text gas additives may be added to the test gas to determine their effect upon fracturing and/or to determine the chemical take-up of those additives from flowing across the pre or post fractured material sample. In an embodiment, surfactants, lubricants and/or condensed phases may be added to the test gas After removal from the text device, the material sample may be visually, chemically and mechanically analyzed for fracture characteristics such as, but not limited to fracture length, width, shape, branching, mineralogic changes, recrystallization, melt, pore characteristics, chemical modifications and other sample characteristics.

The invention being thus described, it will be obvious that the same may be varied in many ways. Such variations are not to be regarded as a departure from the spirit and scope of the invention, and all such modifications as would be obvious to one skilled in the art are intended to be included within the scope of the appended claims. It is intended that the scope of the invention be defined by the claims appended hereto. The entire disclosures of all references, applications, patents and publications cited above are hereby incorporated by reference.

In addition, many modifications may be made to adapt a particular situation or material to the teachings of the disclosure without departing from the essential scope thereof. Therefore, it is intended that the disclosure not be limited to the particular embodiment disclosed as the best mode contemplated for carrying out this disclosure, but that the disclosure will include all embodiments falling within the scope of the appended claims.

What is claimed is:

1. A device for electrofracturing a material sample, comprising:
   a pressure vessel comprising an internal cavity;
   a pressurized fluid supply system fluidly coupled to the internal cavity;
   a material sample disposed within the internal cavity;
   a voltage source electrically coupled to the material sample to provide a voltage pulse across the material sample; and
   a gas measurement system fluidly coupled to the material sample;
   wherein the voltage source provides a pulse of between 150 kv and 1 MV.

2. The device of claim 1, wherein the pressurized fluid system is capable of pressurizing the internal cavity up to 20,000 psi.

3. The device of claim 1, wherein the voltage source provides a pulse of 1 MV.

4. The device of claim 1, wherein the voltage source provides a pulse of 200 kV.

5. The device of claim 1, wherein the voltage source is capable of providing a pulse having a pulse width of between 100 picoseconds (ps) and 1 day.

6. The device of claim 1, wherein the gas measurement system comprises a mass spectrometer.

7. The device of claim 1, wherein the gas measurement system comprises a flow meter.

8. The device plate of claim 1, wherein the material sample is shale.

9. The device of claim 1, wherein the material sample is disposed with a test assembly disposed within the internal cavity, the test assembly comprising:
   a first nonconductive end cap on a first surface of the material sample;
   a second nonconductive end cap on a second surface of the material sample opposite the first surface;
   a first and second conductors passing through the first and second nonconductive end caps, respectively, and contacting the material sample; and a jacketing material sealing the material sample between the first and second nonconductive end caps.

10. A method of electrofracturing a material sample, comprising:
providing a material sample;
subjecting the material sample to an external pressure;
subjecting the material sample to a voltage potential;
flowing a test fluid across the material sample; and
measuring the amount of test gas that flows from the material sample;
wherein the voltage potential is between 150 kv and 1 MV.

11. The method of claim 10, further comprising:
determining the permeability of the material sample.

12. The method of claim 10, wherein the external pressure is between 2,000 psi and 20,000 psi.

13. The method of claim 10, wherein the voltage potential is capable of fracturing the material sample.

14. The method of claim 10, wherein the voltage potential is pulsed two or more times and the time between pulses is 100 μs to 1 day.

15. The method of claim 10, wherein the voltage potential has a pulse width of between 100 picoseconds (ps) and 1 day.

\* \* \* \* \*